United States Patent [19]

Faber et al.

[11] Patent Number: 4,567,145

[45] Date of Patent: Jan. 28, 1986

[54] CONTINUOUS PRODUCTION OF ETHANOL BY USE OF RESPIRATION DEFICIENT MUTANT YEAST

[75] Inventors: Marcel Faber, Princeton, N.J.; Jerome D. Bernstein, New Hope, Pa.; Matthew Grossman, Piscataway, N.J.

[73] Assignee: HRI, Inc., Gibbsboro, N.J.

[21] Appl. No.: 441,474

[22] Filed: Nov. 15, 1982

[51] Int. Cl.$^4$ ............................ C12P 7/06; C12N 1/16
[52] U.S. Cl. ..................................... 435/161; 435/255; 435/940
[58] Field of Search ........................ 435/161, 940, 255

[56] References Cited

U.S. PATENT DOCUMENTS 4,368,268  1/1983  Gong ................................... 435/161

OTHER PUBLICATIONS

Righelato et al., Chem. Abst., vol. 94 (1981), p. 101,297y.
Faust et al., Chem. Abst., vol. 94 (1981), p. 207,162r.

Primary Examiner—Sam Rosen
Attorney, Agent, or Firm—Fred A. Wilson

[57] ABSTRACT

This invention provides a process for producing ethanol from a D-sugar in a continuous aerobic environment using a flocculant respiration-deficient mutant of *Saccharomyces uvarum* in a single stage fermentor with a cell settling tank and cell recycle, at a productivity of more than 50 grams ethanol per liter fermentor volume per hour. The process comprises (a) innoculating a fermentation zone with a respiration-deficient mutant of *Saccharomyces uvarum;* (b) feeding a mixture of a D-sugar, a nitrogen source, a vitamin source and a mineral source into the fermentation zone in the presence of oxygen, and (c) fermenting the D-sugar mixture for a sufficiently long period of time to yield an ethanol product. In the process, the yeast are allowed to settle for a sufficiently long period of time and recycled to the fermentation zone to increase ethanol productivity. The preferred D-sugar that may be used in the present process to produce ethanol, is D-glucose.

18 Claims, 1 Drawing Figure

CONTINUOUS PRODUCTION OF ETHANOL BY USE OF RESPIRATION DEFICIENT MUTANT YEAST

BACKGROUND OF INVENTION

This invention relates to a process for producing ethanol. More particularly, it relates to a process for producing ethanol from a D-sugar.

Yeasts of the genus *Saccharomyces* have been found to be generally good alcoholic fermentors, capable of producing ethanol from a variety of naturally occurring D-sugars. *Saccharomyce cerevisiae* is more commonly used for industrial alcohol production. Usual growth requirements for the yeast include a carbon and energy source, which is supplied by the sugar, a nitrogen source which may be supplied as ammonium salts, urea or peptone, and a source of certain vitamins (particularly those of the B-complex), which, if not present in some naturally occurring crude feedstock, can be supplied in the form of a yeast extract. Also required is a mineral source, which, if not present in the naturally occurring feedstock, or water, can be supplied in the form of a yeast extract.

Yeast will generally produce ethanol under two environmental conditions. These conditions are (a) a lack of oxygen (i.e., oxygen-limited conditions) and (b) the presence of a high sugar content. In producing ethanol from D-sugars, there is a need to produce the ethanol in a continuous culture. The continuous culture as yeast cell mandates the continuous propagation of cells. The yeast cell concentration is at a steady state when the rate of cell growth equals the rate at which cells are drained off or die. The cell dilution rate is proportional to the feed-in rate and is equal to the specific growth rate of the organism, i.e., the yeast mutant, in the steady state.

In an industrial continuous fermentation process for the production of ethanol, the sugar concentration in the fermentor effluent should be near zero. However, a continuous fermentation cannot be conducted under completely anaerobic conditions, since oxygen is needed by the yeast as an essential nutrient for growth.

The oxygen control is critical in a continuous ethanol culture especially when using a single fermentor. Too much oxygen results in mitochondrial biogenesis, which leads to oxidative enzyme formation and thus to more yeast cells at the expense of ethanol production. Too little oxygen causes cessation of growth and, therefore, total loss of the continuous culture.

Continuous fermentation to produce ethanol can be conducted with the addition of a small controlled amount of oxygen to the continuous fermentor, with the purpose of keeping the yeast in an active state. This was shown in the study of Cysewski, G. R. and Wilke, C. R., *Biotechnol. Bioeng.* 20 1421 (1978).

In continuous fermentation of D-sugars to ethanol, a high rate of ethanol production per unit of fermentor volume is desirable to limit fermentor size and cost. Fermentors can be made more productive by recycling yeast cells. Ease of separation of the yeast cells from the fermentor effluent is highly desirable to effect this recycle of yeast cells. Traditional strains of *Saccharomyce cerevisiae* are difficult to separate from the fermentor effluent and require the use of expensive centrifugation and filtration equipment. Even the centrifuged yeast has a considerable amount of liquids adhering, which makes the recycle less efficient due to the fact that the recycled ethanol reduces the fermentation rate.

Flocculating strains of the *Saccharomyces* yeast have been developed, which are easier to separate from the fermentor effluent and do not require costly centrifuges.

Respiration-deficient yeast mutants (RDM), also called Rho mutants as described by Aiba, S., Shoda, M., and Nagatine, M., in *Biotechnol. Bioeng.* 10 845 (1968), can ferment glucose to ethanol in the presence of excess oxygen. This has the advantage that oxygen addition need not be controlled precisely and thus alleviates many process control problems. Under normal conditions, in which sufficient aeration is provided, insufficient ethanol production results due to the well documented Pasteur effect, which occurs when glucose is metabolized in a series of reactions which by-pass ethanol production in order to derive the energy needed by the cell. This reaction sequence involves a number of enzymes and is called respiration, since oxygen serves as the terminal electron acceptor in the series of events. In order to avoid the loss of productivity associated with this process, a mutation can be induced in the yeast, which results in the loss of respiratory activity. Such mutants are prepared by a standard procedure first described by Boris Euphrussi [Unites Biologiques Dourees de Continuite Genetique, Paris, June-July, pp. 165–180, Editions du C.M.R.S., Paris (1949)] using acriflavin dye.

This mutation, known as petite due to its effect on colony size, is very stable and allows for ethanol production in an aerobic environment so that the Pasteur effect is avoided.

Aiba, et al demonstrated a rate of ethanol production by a respiration deficient mutant of *Saccharomyce cerevisiae* of only 1.69 grams per liter of fermentor volume per hour. This activity of the Rho mutant was inhibited by an ethanol concentration of 1%. Therefore, the feed glucose concentration could not exceed 20 grams per liter and the ethanol yield could not exceed 10 grams per liter or 1%, which would be difficult if the process were expanded to an industrial scale. Furthermore, the cell dry mass obtained in this system was only 2.3 grams per liter.

The above study tends to indicate that respiration-deficient mutants (RDM) cannot be advantageously used to industrially produce ethanol from a D-sugar. However, as discussed below, by the present invention it was found that a respiration-deficient mutant (RDM) strain of *Saccharomyces uvarum* tends to produce a a high yield of ethanol in the presence of air.

SUMMARY OF INVENTION

This invention provides a continuous process for producing ethanol from D-sugars. This process comprises:
(a) inoculating a fermentation zone with a respiration-deficient mutant of a flocculating strain of *Saccharomyces uvarum*;
(b) feeding a mixture of a D-sugar, a nitrogen source, a vitamin source and a mineral source into the fermentation zone in the presence of an oxygencontaining gas; and
(c) fermenting the D-sugar mixture for a sufficiently long period of time to yield an ethanol product.

The process can be operated on a once-through basis, or with cell recycle. Cell recycle increases the density of the yeast cells in the fermentor, by recycling the yeast cells that are separated from the fermentor effluent, back to the fermentor. This yeast cell recycle increases the productivity of the fermentor in terms of ethanol production per unit of fermentor volume per hour.

In the yeast cell recycle operation, the contents of the fermentation zone, i.e., a homogeneous mixture of spent (sugar-free) liquor, issues therefrom through an overflow arm into a cell settling tank. A recycle loop is arranged so that a sludge of high solids content is recycled back from the bottom of the cell settling tank to the fermentation zone, while an ethanol containing liquid product of low-solids content issues from the cell settling tank overflow arm to be distilled to produce higher purity ethanol.

Also, according to the present process, the harvest of cells may be selected, when appropriate, for other uses than recycle.

The preferred D-sugar in the practice of the present invention is D-glucose.

DETAILED DESCRIPTION OF INVENTION

Figure 1:
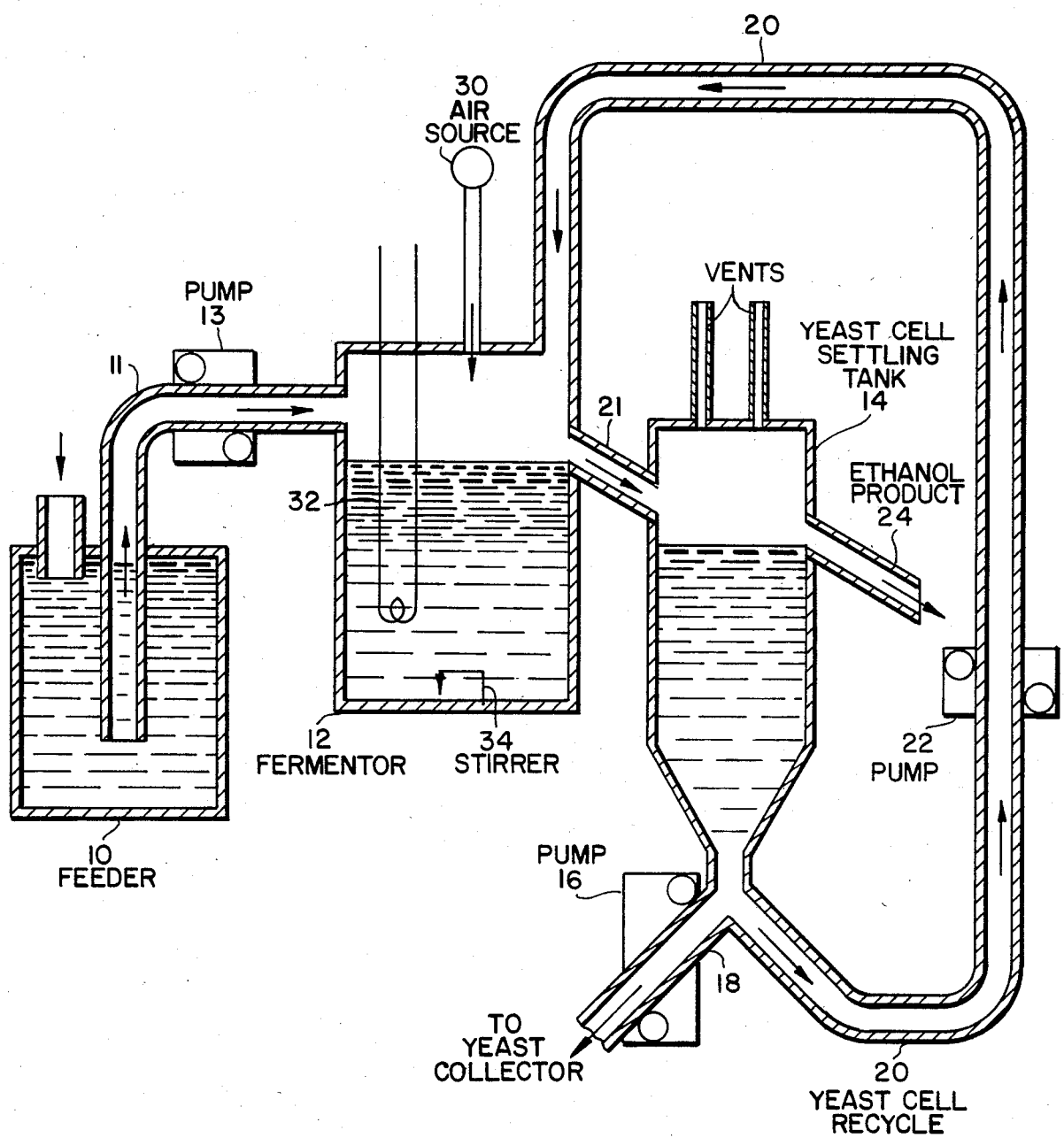
FIG. 1 is a flow diagram of the present fermentation process for producing ethanol, using cell recycle.

In producing ethanol from a D-sugar, the respiration-deficient mutant yeast preferably used is obtained from a flocculating strain of Saccharomyces uvarum. In the fermentation of such D-sugars, the fermentation medium has the same composition as the culture medium except for the variable glucose which is specified. Preferably, the media is sterilized in batch for 30 minutes at 110° C. and 15 psig, or it could be done continuously under these conditions.

The highly flocculant, respiration deficient mutant yeast is produced from a strain of Saccharomyces uvarum ATCC 26602. It has been demonstrated in aerobic batch culture, that the mutant produces alcohol, i.e., ethanol, at a rate about 50% higher than the parent strain. In carrying out the present continuous system, it has been found that: (1) the system remains stable for more than 200 days without any necessary shutdowns, (2) the high flocculance of the yeast allows selective return of a sludge of cells to the fermentation zone, and (3) the mutation remains stable throughout the operation, i.e., over 200 days.

In addition to the mutant strain of Saccharomyces uvarum ATCC 26602, strain of Saccharomyces uvarum ATCC 2345 may be used in the present process for producing ethanol from a D-sugar.

The respiration-deficient mutant (RDM) of the present invention, i.e., mutant of strain ATCC 26602, may be produced by the method described by Susumu Nagai in SCIENCE, Vol. 130, pp. 1188–1189 (October, 1959), for producing a mutant of baker's yeast, which is incorporated by reference. As generally described in this reference, acriflaven dye as well as other dyes can be advantageously used to induce the formation of petite colonies of the yeast mutant.

As illustrated in FIG. 1, in carrying out the present continuous process in a system with cell recycle, initially the feed material pumped from the feeder 10 into the fermentation zone, i.e., fermentor 12, is inoculated with a sufficient mass of cells of the respiration-deficient mutant of Saccharomyces uvarum ATCC 26602. The feed material is pumped through line 11 by a peristalic pump 13 into the fermentor 12 having a volume of 350 ml. The fermentor is thermostatted by coil 32 to maintain the feed material at the desired temperature. The fermentor 12 contents are sparged with oxygen-containing gas (e.g., air), provided from an air source 30, and agitated with a stirrer 34.

The material from fermentor 12 is overflowed through line 26 into a cell settling tank 14 having a volume of 600 ml and a vent 15. A portion of fermented material which contains a low yeast content overflows from the settling tank 14 as a product ethanol through line 24. Another portion which contains a high content of yeast is recycled through line 20 by a second peristaltic pump 22 back to the fermentor 12 where it is fermented further to provide the ethanol product. The remaining portion containing yeast is withdrawn through line 18 to a yeast collector by a third peristaltic pump 16.

Specifically, in carrying out the present continuous process for producing ethanol, D-glucose may be fed into the fermentation zone, i.e., fermentor 12, with air in the presence of a respiration deficient yeast mutant, i.e., a mutant of a flocculating strain of Saccharomyces uvarum. To this D-glucose combination, there may also be added a nitrogen-containing material, i.e., a nitrogen source, a vitamin and a mineral source to effectively support the growth of the yeast mutant. Then, the mixture of D-glucose, nitrogen-source, vitamin source and mineral source is allowed to ferment in fermentor 12 for a sufficient length of time to yield an ethanol product. In the process, the yeast are allowed to settle in the settling tank 14 for a sufficiently long period of time and then recycled to the fermentation zone, i.e., fermentor 12, to substantially increase the productivity of ethanol.

The usual growth requirements of yeast includes an organic carbon compound (i.e., which could consist of one or more sugars) which serves as both a source of carbon to build other molecules for the growing cell and as an energy source. Also required for this growth is a nitrogen source, inorganic or organic. This is typically supplied in the form of ammonium salts, urea or peptone, an enzymatically prepared hydrolyzate containing nitrogen in a utilizable form.

According to the present invention, the use of the respiration-deficient mutant (RDM) obviates the need for having multistage fermentors in series. The usual practice in continuous ethanol production is to have up to eight (8) fermentors in series, the first several of which are aerated for the purpose of producing more cells; and the later fermentors operate anaerobically for the purpose of producing ethanol by the cells. The use of the respiration-deficient mutant (RDM) eliminates the need for multi-stage fermentors since oxygen is added for cell growth without adverse effects upon ethanol production.

Many strains of yeast such as those that can be used in the present process, grow better in the presence of minerals, and certain vitamins, particularly those of the B-complex, which are often provided in the form of a yeast extract. Both the peptone and the yeast extract also supply required minerals and trace elements which would otherwise be added individually.

Both the vitamin and mineral sources for the present process may be provided by a yeast extract sold under the name of "Difco Certified" Bacto Yeast Extract, and manufactured by Difco Laboratories of Detroit, Mich.

Oxygen is also a growth requirement, generally provided by sparging the fermentor with air to provide adequate gas transfer at the liquid surface.

Yeast can be grown in a continuous process, which is useful when one considers the large volumes of yeast that would be required by the alcohol fuel industry. In a continuous culture, feed material is pumped into the fermentor at a fixed rate and spent liquid containing cells and alcohol issues from an overflow arm at an equal rate. In the fermentor, the temperature, pH, stirring or agitation and aeration rates are generally maintained at constant values by standard automated procedures. A variety of biological "steady-states" are obtained when the sugar is used up immediately as it enters the fermentor and when the growth rate matches the dilution rate such that cell density remains constant and the cells remain in a metabolically active state. The ethanol production rate also remains constant. The feed D-sugar concentration and dilution rate can be manipulated in order to maximize ethanol production at some ceiling value in which steady-rate conditions still hold in that system. The function of cell recycle may also be used as another established technique towards this objective, by returning active cells to the fermentor, to maintain a higher cell-density therein.

The feed medium used according to the present process, may contain D-glucose, a yeast extract and peptone. The glucose is used immediately as it enters the fermentor 12 since it is the limiting agent for the fermentation. This is a characteristic of the steady state condition as described above. The result is that the fermentor glucose concentration is always near zero.

In carrying out the present process, the D-sugars that may be utilized are selected from groups consisting of monosaccharides (e.g., glucose, galactose and fructose), disaccharides (e.g., maltose, sucrose and melibiose) and trisaccharides such as raffinose. Cane molasses and starch hydrolyzates are examples of the various sugars that may be utilized in this process.

According to the present process, the fermentation startup involves inoculation of the fermentor with a sufficient mass of cells of the respiration-deficient mutant of *Saccharomyces uvarum*. In the ethanol production, a feedstock containing between about 110 and about 150 grams per liter of D-glucose, 1% peptone, and 0.5% yeast extract, at pH 2.5 (HCL), sterilized at 110° C., 15 psig, 30 minutes, is fed into the fermentation zone at a rate of 5.0 to 5.5 ml per min. The fermentator 12 (350 ml volume) is sparged with air (about 0.4 liters per minute), stirred at 500 R.P.M., thermostatted at a temperature of between about 30° and about 35° C. and maintained at a pH of 4.0 by automatic titration. Overflow from the fermentor is run into a cell settling tank 14 of 600 ml volume, from which a sludge of settled cells and broth is pumped back into the fermentor at an appropriate rate. At the optimal cell recycle rate a sludge selectively high in solids is returned to the fermentor, but not so high as to clog the system or necessitate shutdown. A beer or lower solids content ethanol product issues from an overflow arm in the cell settling tank for collection. Glucose is converted to ethanol in a range of from about 4.0 to about 7.0 w/v% and a productivity value in excess of 50 grams of ethanol per liter fermentor volume per hour. Such a productivity is high when compared with other strains of *Saccharomyces uvarum* or *Saccharomyce cerevisiae* when used in a continuous system with cell recycle. It should be noted that the productivity reported herein is based on the effective volume of the fermentor. The overflow from the fermentor contains less than 0.1 grams of glucose per liter. This low glucose content indicates that the fermentation is essentially complete in the fermentation vessel 12.

The following examples will illustrate more fully the advantage of the present process.

EXAMPLE 1

Batch Fermentation Using A Parent Strain Of A Flocculant *Saccharomyces Uvarum*

In order to determine the ethanol productivity of the mutant yeast and its effectiveness in ethanol production, initially the parent strain of *Saccharomyces uvarum* ATCC 26602 was tested for its ability to produce ethanol under predetermined conditions as a control.

In this first test, the fermentor of a continuous fermentation system was charged with 350 ml of the sterilized medium containing 245 grams per liter glucose, 1% peptone and 0.5% yeast extract and inoculated with the parent strain *Saccharomyces uvarum* ATCC 26602. The mixture was maintained at a pH 4.5 (by automatic titration), at 32° C., was sparged with air at 0.4 liters of air per minute and stirred at 500 R.P.M. The mixture was allowed to ferment until depletion of the glucose in the wort, at which time, after 48 hours, the ethanol content was determined to be 21.4 grams or a yield of 48.8% of the theoretical yield.

EXAMPLE 2

Batch Fermentation Using The Respiratory-Deficient Mutant Of The Flocculant Strain Of *Saccharomyces Uvarum*

In order to compare the ethanol productivity of the mutant yeast relative to the parent, the fermentator of the continuous system was charged with 350 ml of a similar medium (i.e., 230 grams per liter glucose) but inoculated with the mutant strain.

The mixture was fermented as described above in Example 1, until depletion of glucose at which time after 48 hours ethanol contents were determined to be 29.4 grams, representing a yield of 71.5% of the theoretical yield.

The results clearly indicate that the mutant produced ethanol with a yield 46% greater than the yield obtained with the parent strain, which indicates the respiration-deficient character of this mutant yeast.

EXAMPLE 3

Continuous Fermentation Using The Respiration Deficient Mutant Of The Flocculant Strain Of *Saccharomyces Uvarum*

Because of the high productivity the yeast mutant demonstrated in batch fermentation as shown in Example 2, the mutant was then used in a continuous fermentation as follows.

Similar to the process described in Examples 1 and 2, the fermentor was charged with 350 ml of a sterilized feed medium containing 135 grams per liter glucose, 1% peptone, 0.5% yeast extract, pH 4.0, and inoculated with the Rho mutant of *Saccharomyces uvarum* ATCC 26602. The mixture was maintained at pH 4.0 (by automatic titration), at 32° C., was sparged with 0.4 liters of air per minute and was stirred at 500 R.P.M. For complete utilization of glucose, a maximal feed rate of 0.75 ml per minute (or a dilution rate of 0.129 hr$^{-1}$) was achievable. Ethanol was produced to achieve a concentration of 5.3 w/v %, representing a productivity of 6.7 grams ethanol per liter fermentor volume per hour and a yield of 75% of the theoretical yield. A dry cell density of about 10 grams per liter was achieved in steady state operation.

EXAMPLE 4

Continuous Fermentation Using The Respiration Deficient Mutant Of The Flocculant Strain Of *Saccharomyces Uvarum* And Cell-Recycle In order to improve the ethanol productivity of the continuous fermentation system with the yeast mutant still further, a cell recycle apparatus was incorporated into the continuous fermentation system as shown in FIG. 1.

A continuous fermentation system identical to that described in Example 3 except for the addition of the cell recycle apparatus was similarly charged with an identical feed mixture, inoculated with the Rho mutant of *Saccharomyces uvarum* ATCC 26602, maintained at a pH of 4.0 and 32° C., sparged with air and stirred. For complete glucose utilization in the fermentor, a maximal feed rate of 5.5 ml per minute (or a dilution rate of about 0.94 hour$^{-1}$) was utilized when a dry cell density of about 50 grams per liter was reached in steady state operation. Ethanol was produced to achieve a concentration of 6.0 w/v%, representing a productivity of 55.8 grams ethanol per liter fermentor volume per hour and a yield of 86% of the theoretical yield.

The interfacing of the cell recycle unit (i.e., as shown in FIG. 1) therefore allowed for the achievement of more than a five-fold increase in ethanol productivity relative to the system in the absence of the cell recycle unit.

We claim:

1. A continuous process for producing ethanol from D-sugars, comprising:
   (a) inoculating a fermentation zone with a respiration-deficient mutant of a flocculating strain of *Saccharomyces uvarum*;
   (b) feeding a mixture of a D-sugar, a nitrogen source, a vitamin source and a mineral source into said fermentation zone in the presence of an oxygen-containing gas;
   (c) fermenting said D-sugar mixture for a sufficiently long period of time to yield an ethanol product; and
   (d) separating said ethanol product as overflow from the mutant yeast cells.

2. The process according to claim 1, wherein said D-sugar is selected from the group consisting of monosaccharides, disaccharides and trisaccharides.

3. The process according to claim 1, wherein said D-sugar is selected from the group consisting of glucose, galactose, fructose, maltose, sucrose, melibiose and raffinose.

4. The process according to claim 1, wherein said D-sugar is D-glucose.

5. The process according to claim 1, wherein the feed concentration of said D-sugar ranges from about 110 to about 150 grams/liter.

6. The process according to claim 1, wherein said oxygen containing gas is air or oxygen.

7. The process according to claim 1, wherein said nitrogen source is ammonium salts, urea or peptone.

8. The process according to claim 1, wherein the fermentation takes place at a temperature ranging from about 30° to about 35° C.

9. The process according to claim 1, wherein the rate of flow of oxygen-containing gas is about 0.4 liters/minute.

10. The process according to claim 1, wherein the pH of the fermentation zone is about 4.0.

11. The process according to claim 1, wherein the cells of said mutant are recycled back into said fermentation zone to increase the productivity of ethanol by more than five-fold.

12. The process according to claim 1, wherein the ethanol product contains from about 4.0 to about 7.0 w/v % ethanol.

13. The process according to claim 1, wherein the ethanol productivity is more than 5 grams of ethanol per liter of fermentor volume per hour without cell recycle.

14. The process according to claim 11, wherein the ethanol productivity is more than 50 grams of ethanol per liter of fermentor volume per hour, with cell recycle.

15. The process according to claim 1, wherein said D-sugar is provided by molasses.

16. A respiration deficient mutant of *Saccharomyces uvarum* strain ATCC 26602 for producing ethanol from D-sugar.

17. A continuous process for producing ethanol from D-suagrs selected from the group consisting of monsaccharides, disaccharides and trisaccharides, the process comprising:
   (a) inoculating a fermentation zone with a respiration-deficient mutant of a flocculating strain of *Saccharomyces uvarum*;
   (b) feeding a mixture of said D-sugar, a nitrogen source, a vitamin source and a mineral source into said fermentation zone in the presence of an oxygen-containing gas;
   (c) fermenting said D-sugar mixture for a sufficiently long period of time to yield an ethanol product;
   (d) overflowing said ethanol product and yeast mutant cells from said fermentation zone into a cell settling zone and withdrawing the ethanol product as overflow from the settling zone; and
   (e) recycling cells of said mutant back to the fermentation zone to increase the productivity of ethanol to more than about 50 grams ethanol per liter of fermentation zone volume per hour.

18. A continuous process for producing ethanol from substantially D-glucose feed material, the process comprising:
   (a) inoculating a fermentation zone with a respiration-deficient mutant of a flocculating strain of *Saccharomyces uvarum* yeast;
   (b) feeding a mixture of said D-glucose, a nitrogen source, a vitamin source and a mineral source into said fermentation zone in the presence of an oxygen-containing gas, said D-glucose having a feed concentration of about 110–150 gram/liter;
   (c) fermenting said D-glucose mixture at about 30°–35° C. temperature for a sufficiently long period of time to yield an ethanol product;
   (d) overflowing said ethanol product and yeast mutant cells from said fermentation zone into a cell settling zone and withdrawing the ethanol product containing about 4.0–7.0 W% ethanol as overflow from the settling zone; and
   (e) recycling cells of said mutant and broth back to the fermentation zone to increase the productivity of ethanol to more than about 50 grams ethanol per liter of fermentation zone volume per hour.

* * * * *